(12) United States Patent
Kim et al.

(10) Patent No.: US 8,453,639 B2
(45) Date of Patent: Jun. 4, 2013

(54) AUTOMATIC VIDEO INSTILLATOR

(75) Inventors: Jin-Sung Kim, Daejeon (KR); Bae Lee, Seoul (KR); In-Cheol Hwang, Seoul (KR); Chang-Woo Song, Daejeon (KR); Sang-Seop Han, Daejeon (KR)

(73) Assignees: Korea Research Institute of Chemical Technology, Daejeon (KR); Doobae System, Seoul (KR)

( * ) Notice: Subject to any disclaimer, the term of this patent is extended or adjusted under 35 U.S.C. 154(b) by 927 days.

(21) Appl. No.: 12/531,823

(22) PCT Filed: Mar. 4, 2008

(86) PCT No.: PCT/KR2008/001229
§ 371 (c)(1),
(2), (4) Date: Sep. 17, 2009

(87) PCT Pub. No.: WO2008/117940
PCT Pub. Date: Oct. 2, 2008

(65) Prior Publication Data
US 2010/0101569 A1     Apr. 29, 2010

(30) Foreign Application Priority Data
Mar. 26, 2007  (KR) ................... 10-2007-0029398

(51) Int. Cl.
*A61M 16/00*  (2006.01)
*A61B 1/00*  (2006.01)
*A62B 17/00*  (2006.01)

(52) U.S. Cl.
USPC ............ 128/200.26; 128/202.27; 128/207.14; 128/207.15; 604/46; 604/131; 600/109; 600/110; 600/118; 600/120; 600/122

(58) Field of Classification Search
USPC   128/200.26, 202.27, 207.14, 207.15; 604/46, 604/131; 600/109, 110, 118, 120, 122
See application file for complete search history.

(56) References Cited

U.S. PATENT DOCUMENTS
5,337,731 A * 8/1994 Takahashi et al. ............ 600/109
(Continued)

FOREIGN PATENT DOCUMENTS
EP             937478 A1 * 8/1999
WO   WO-2004/062713 A1   7/2004
(Continued)

OTHER PUBLICATIONS
Written Opinion and International Search Report dated May 20, 2008. PCT/KR2008/001229. 5 pages.

*Primary Examiner* — Clinton T Ostrup
(74) *Attorney, Agent, or Firm* — Gifford, Krass, Sprinkle, Anderson & Citkowski, P.C.

(57) ABSTRACT

An automatic video instillator that can accurately and easily administer inhalation into an airway of an animal by providing images of a throat is provided. An automatic video instillator includes a case defining a space, a guide unit that protrudes frontward from the case to secure an airway of an animal by being inserted through a throat of the animal, an image pickup unit that is installed on a front end of the guide unit to capture images of portions in front of the guide unit, an administration unit that is installed through the case and the guide unit to administer an inhalation, an administration switch for adjusting administration of a predetermined amount of the inhalation directed to the administration unit into the airway of the animal, and an image display unit that is connected to the image pickup unit to allow a user to see the images captured by the image pickup unit.

21 Claims, 7 Drawing Sheets

U.S. PATENT DOCUMENTS

| | | | |
|---|---|---|---|
| 5,672,155 A * | 9/1997 | Riley et al. | 604/154 |
| 6,638,212 B1 * | 10/2003 | Oshima | 600/109 |
| 6,652,453 B2 * | 11/2003 | Smith et al. | 600/188 |
| 6,929,600 B2 * | 8/2005 | Hill | 600/120 |
| 6,929,619 B2 * | 8/2005 | Fago et al. | 604/67 |
| 2003/0208157 A1 * | 11/2003 | Eidson et al. | 604/131 |
| 2005/0093974 A1 * | 5/2005 | Hibi et al. | 348/71 |
| 2007/0074720 A1 * | 4/2007 | Schwartz et al. | 128/200.26 |
| 2008/0236575 A1 * | 10/2008 | Chuda | 128/200.26 |

FOREIGN PATENT DOCUMENTS

| | | |
|---|---|---|
| WO | WO-2005/039675 A1 | 5/2005 |
| WO | WO-2005/084523 A1 | 9/2005 |

* cited by examiner

AUTOMATIC VIDEO INSTILLATOR

CROSS-REFERENCE TO RELATED APPLICATIONS

This application is the U.S. national phase of PCT/KR2008/001229 filed Mar. 4, 2008, which claims priority of Korean Patent Application No. 10-2007-0029398 filed Mar. 26, 2007.

TECHNICAL FIELD

The present invention relates to an instillator. More particularly, the present invention relates to an automatic instillator that is designed to accurately and easily administer a predetermined amount of inhalation to an animal.

BACKGROUND ART

Generally, in a process for developing medical supplies, agricultural chemicals, and the like, a pre-clinical demonstration (or non-clinical demonstration) is performed on animals such as rodents (e.g., mice and rats) and primates (e.g., monkeys) before a clinical demonstration is performed on human bodies. In a medical treatment of animals, an inhalation such as a test material and medicine is administered thereto. In order to administer the inhalation to the animals, an oral medication method, a non-vein medication method, an inhalation medication method, or the like is used.

A drip-feeding method is known as an inhalation medication method. In the drip-feeding method, an instillator for drip-feeding a liquid inhalation and liquid medicine into an airway of an animal has been used for the purpose of performing the pre-clinical demonstration and treating respiratory organs.

In order to administer the inhalation, the airway of the animal is sufficiently secured by a laryngoscope or an endoscope, after which the inhalation is administered using a drip feeder such as a syringe or a tube. However, in the conventional drip-feeding method, a device for securing the airway and a drip feeder for drip-feeding the inhalation device are necessary. In addition, since a process for securing the airway and a process for administering the inhalation are not clearly visible to the naked eye, it is difficult to accurately administer the inhalation into the airway of the animal. Therefore, the drip-feeding success rate of the inhalation is not high. In addition, it takes a long time to acquire drip-feeding skill.

DISCLOSURE

Technical Problem

The present invention has been made in an effort to solve the limitations of the conventional method and device, and it is an object of the present invention to provide an automatic video instillator that can accurately and easily administer inhalation into an airway of an animal by providing throat images.

Technical Solution

In an exemplary embodiment of the present invention, an automatic video instillator includes a case defining a space, a guide unit that protrudes frontward from the case to secure an airway of an animal by being inserted through a throat of the animal, an image pickup unit that is installed on a front end of the guide unit to take images of portions in front of the guide unit, an administration unit that is installed through the case and the guide unit to administer an inhalation, an administration switch for adjusting administration of a predetermined amount of the inhalation directed to the administration unit into the airway of the animal, and an image display unit that is connected to the image pickup unit to allow a user to see the images taken by the image pickup unit.

The guide unit is detachably installed on the case and formed in a straight shape or a curved shape so that it can effectively feed the inhalation to test animals (e.g., rodents or primates), pets, and the like.

A pushing member for further pushing the administration unit frontward of the guide unit is provided in the case.

The image display unit is integrated with the case or separately provided and connected to the case, and a stand for supporting the automatic video instillator on the floor is provided on the case.

Advantageous Effects

According to the automatic video instillator of the present exemplary embodiment, when the device is inserted into the airway of the animal via the throat for the administration of the inhalation into the airway of the animal, the user can see the video image of the device insertion process. Therefore, the user can sufficiently secure the airway of the animal and accurately administer a predetermined amount of the inhalation into the airway.

BEST MODE

An exemplary embodiment of the present invention will hereinafter be described in detail with reference to the accompanying drawings.

Figure 1:
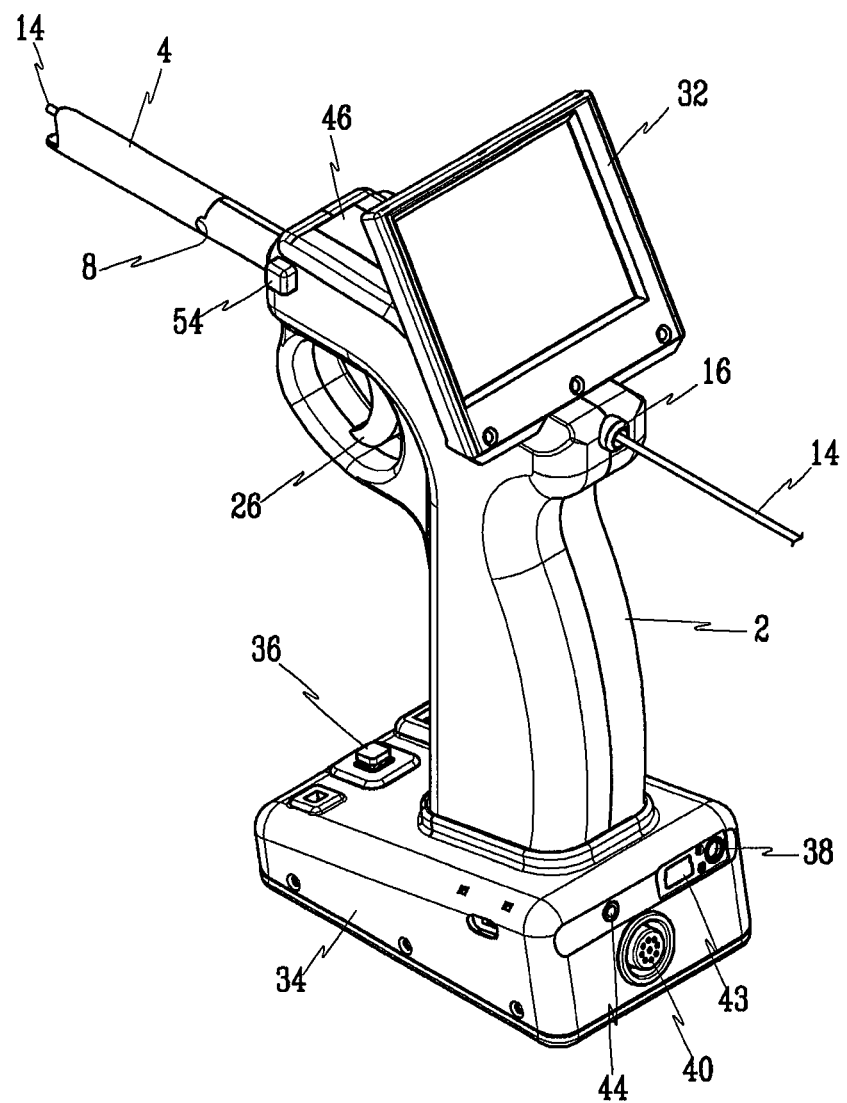
FIG. 1 is a perspective view of an automatic video instillator according to an exemplary embodiment of the present invention.
Figure 2:
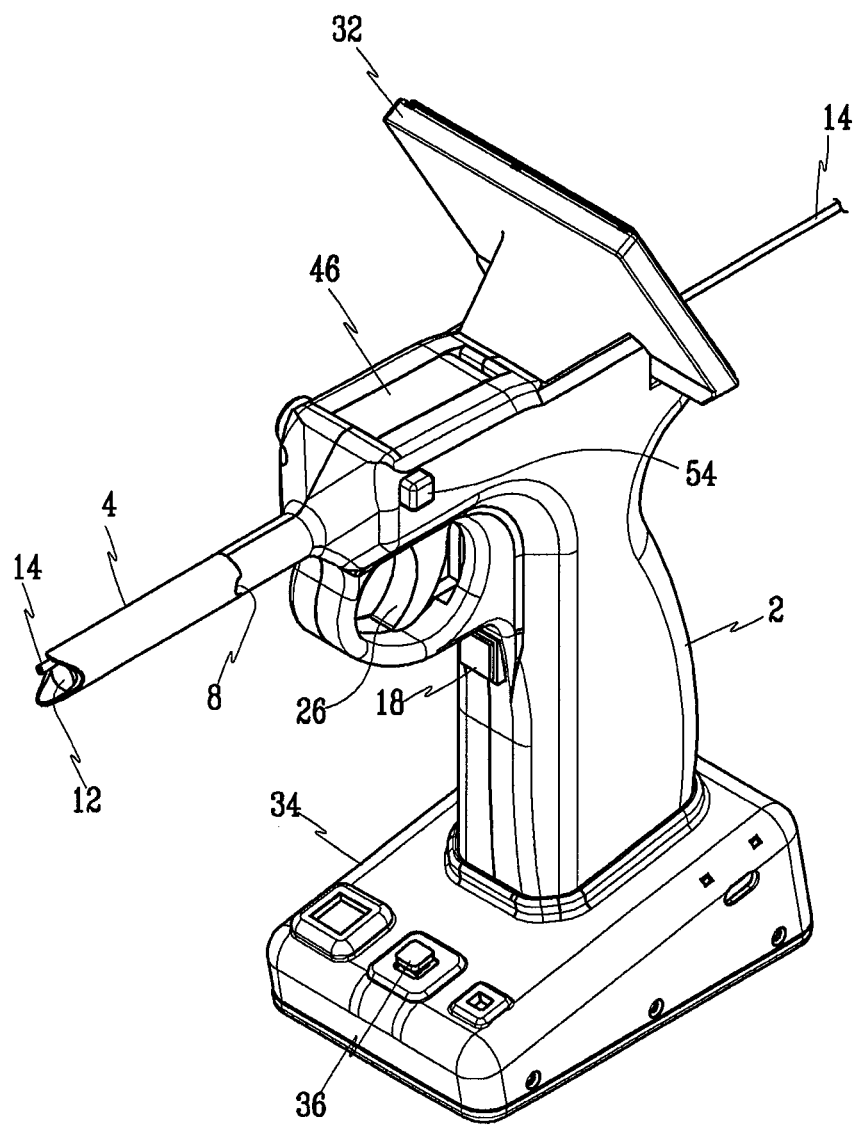
FIG. 2 is a rear perspective view of the automatic video instillator of FIG. 1.

FIG. 1 is a perspective view of an automatic video instillator according to an exemplary embodiment of the present invention, and FIG. 2 is a perspective view of the automatic video instillator of FIG. 1 taken in a different direction. Reference number 2 indicates a case defining an exterior of an automatic video instillator. A variety of components are installed in the case 2.

The case 2 defines a vertical space in which a variety of components can be installed and arranged from the bottom for convenience in use. A guide unit 4 is detachably coupled to a front end of the case 2. A fixing unit 8 for detachably fixing the guide unit 4 to the case 2 is formed on the guide unit 4.

Figure 3:
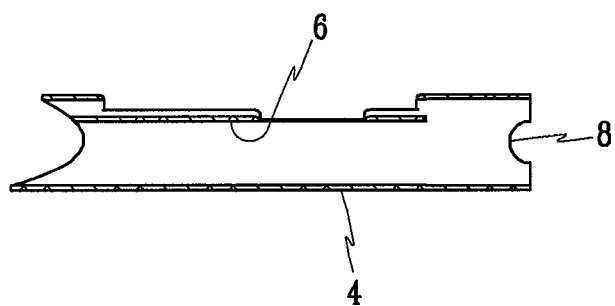
FIG. 3 is a schematic view of a guide unit of an automatic video instillator according to an exemplary embodiment of the present invention.

The guide unit 4 protrudes frontward of the case 2 so that it can secure an airway of an animal by being inserted into a throat of the animal. As shown in FIG. 3, the guide unit 4 is divided by a barrier rib 6 into upper and lower sections. The guide unit 4 includes an administration member and an image pickup member that are installed and supported in the upper and lower sections, respectively.

When the guide unit 4 is detachably mounted on the case 2 as described above, it is easy to wash and sterilize the guide unit 4 when it is detached. In addition, different types of the guide units 4 can be used by being coupled to the case 2 in accordance with a species of animal.

A passageway from a throat to an airway is straight for rodents but curved for primates. Therefore, guide units 4 and 4a may be formed in a straight shape and a curved shape, respectively.

Figure 4:
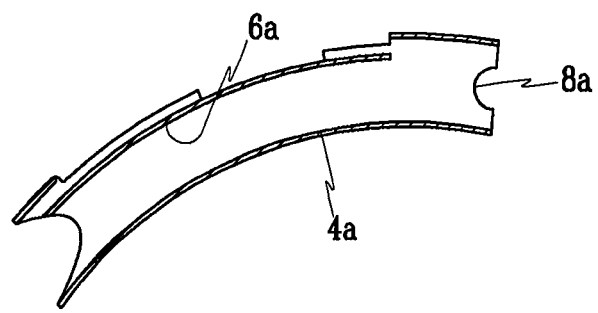
FIG. 4 is a schematic view of a guide unit of an automatic video instillator according to another exemplary embodiment of the present invention.

That is, the guide unit 4 that is formed in the straight shape as shown in FIGS. 1 and 3 may be used to administer inhalation to rodents. The guide unit 4a that is formed in the curved shape as shown in FIG. 4 may be used to give the inhalation to animals such as dogs or monkeys.

Members installed in the guide units 4 and 4a are detachably mounted so that they can be separated from the guide unit when the guide unit is replaced.

Since the components installed in the guide unit 4 that is straight are same as those installed in the guide unit 4a that is curved, the following will exemplarily describe only the guide unit 4 that is straight.

The guide unit 4 includes an image pickup unit 12 for taking front images when the guide unit 4 enters the throat of the animal to drip-feed the inhalation, and an administration unit 14 for guiding the inhalation into the airway.

The image pickup unit 12 includes an image guide and a micro light that provides sufficient illumination for capturing an image. The image guide may be one of an electronic image pickup device (e.g., a charge coupled device (CCD) or a complementary metal oxide semiconductor (CMOS)) and an optical fiber. In the present exemplary embodiment, one of the CCD, CMOS, and optical fiber may be selectively used. Since the CCD, CMOS, and optical fiber are well known in the art and are commercially available, detailed description thereof will be omitted herein.

The image pickup unit 12 is mounted such that a front end thereof is located in the guide unit 4. The images taken by the image pickup unit 12 may be stored in a storage media and/or output to an external side through a cable.

The administration unit 14 defines a passageway through which the inhalation is administered to the animal. The administration unit 14 is formed of a flexible, elastic material. For example, the administration unit 14 may be a plastic tube or a fused silica capillary. When the administration unit 14 is the fused silica capillary, the diameter thereof can be reduced.

The administration unit 14 includes a first end located on the front end of the guide unit 4 and a second end extending to an external side through a support 16 formed on an outer side of the case 2. The second end of the administration unit 14 is connected to a syringe pump (not shown) or a dispenser (not shown) storing the inhalation.

A program for adjusting a flow rate and operation time is built into the syringe pump or dispenser. A condition corresponding to a desired amount of inhalation that will be administered into the airway of the animal is set in the program. Since the syringe pump and dispenser are commercially available, detailed description thereof will be omitted herein.

The administration unit 14 is connected to an administration switch 18 that is used to administer a predetermined amount of the inhalation into the airway via the throat of the animal. The syringe pump or dispenser delivers the predetermined amount of inhalation to the administration unit 14 in response to an operation start signal from the administration switch 18.

In order to secure a more accurate administration location when the inhalation is drip-fed into the airway of the animal, a pushing member 20 for further pushing the administration unit 14 frontward of the guide unit 4 is provided.

Figure 5:
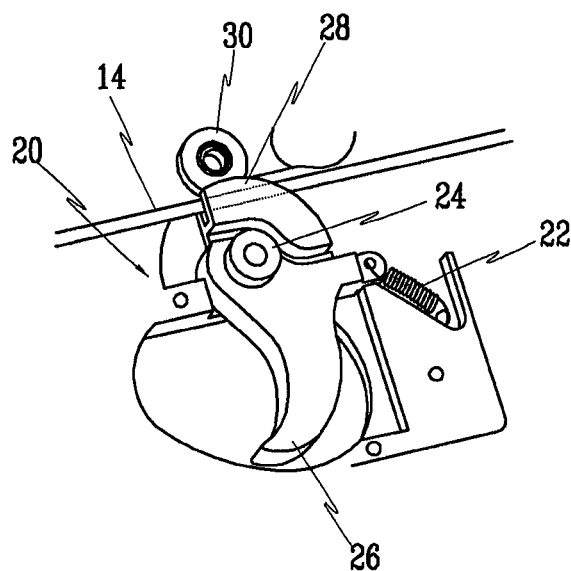
FIGS. 5 and 6 are views of a pushing member of an automatic video instillator according to an exemplary embodiment of the present invention.
Figure 6:
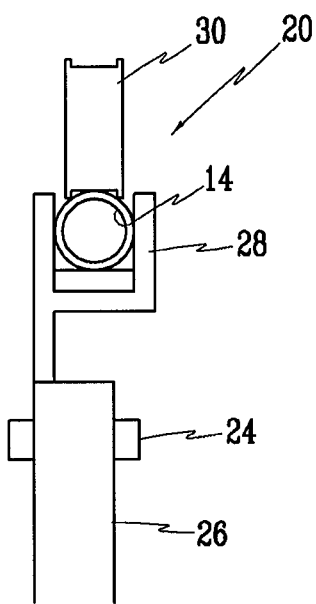

As shown in FIGS. 5 and 6, the pushing member 20 includes a lever 26 that is biased by an elastic member (e.g., a compressed coil spring) 22 and is fixed to the case 2 by a hinge unit 24, an actuating unit 28 that pushes the administration unit 14 while contacting a first surface of the administration unit 14 and being rotated by the operation of the lever 26, and a supporting wheel 30 supporting a second surface of the administration unit 14.

The actuating unit 28 is integrally formed with the lever 26 and provided with a groove having a predetermined curvature, in which the administration unit 14 is inserted and supported. The actuating unit 28 and the supporting wheel 30 are formed of rubber or silicon that has a relatively high frictional force.

The supporting wheel 30 is an idle wheel that can freely rotate by being hingedly fixed to the case 2. The administration unit 14 is interposed between the actuating unit 28 and the supporting wheel 30.

When the lever 26 is pulled, the lever 24 rotates about an axis of the hinge unit 24 while overcoming the biasing force of the elastic member 22. By the rotation of the lever 26, the actuating unit 28 rotates to push the administration unit 14 out of the front end of the guide unit 4 by a predetermined distance.

By pushing the administration unit 14, the administration unit 14 is further advanced frontward from the guide unit 4 and is thus inserted into the airway in a state where the guide unit 4 secures the throat of the animal. As a result, the inhalation can be more accurately administered into the airway of the animal.

When the lever 26 is released after the inhalation is administered, the lever 26 reversely rotates about the axis of the hinge unit 24 by the biasing force of the elastic member 22 and thus the actuating unit 28 rotates. As a result, the administration unit 14 returns to its initial position.

As described above, the administration unit 14 is designed to slide frontward by the actuating unit 28 rotating together with the lever when the lever 26 is pulled. However, the present invention is not limited to the above configuration. For example, the administration unit 14 may be advanced and retracted by being forcedly pushed or pulled from the outside.

Alternatively, the lever and actuating unit may be designed in a gear structure so that the administration unit is advanced and retracted as the actuating unit rotates about the axis of the hinge unit by pulling or releasing the lever.

Alternatively, the actuating unit may rotate by a servo motor. That is, when the lever is pulled, the servo motor is driven to rotate the actuating unit to advance the administration unit by a predetermined distance. When the lever is released, the administrating unit returns to the initial position.

In accordance with the above-described automatic video instillator, the guide unit 4 is inserted into the throat of the animal and the image pickup unit 12 captures an image of an administration process and location in the airway. At this point, an image display unit 32 is provided so that a user can administer the inhalation while seeing the image that is captured by the image pickup unit 12.

A monitor formed with a liquid crystal display (LCD) or a cathode ray tube (CRT) may be used as the image display unit 32. The image display unit 32 is connected to the image pickup unit 12 by a cable or wirelessly so that a user can see the images that are captured by the image pickup unit 12. A battery may be used as a power source of the image display unit 32 and the image pickup unit 12.

The image display unit 32 is installed on an outer side of the case 2 in the present exemplary embodiment. However, the present invention is not limited to this configuration. For example, the image display unit 32 may be separately installed and connected to an image output terminal formed on a stand that will be described later by a cable so that the user can see the images. That is, the image display unit 32 may be integrated with the case 2 or detachably mounted on the case 2, or is separated from the case 2.

As the user can secure the airway while seeing the throat of the animal, the user can accurately administer the inhalation into the airway.

A stand 34 may be further provided to easily support the automatic video instillator on a floor.

The stand 34 has a bottom surface having a predetermined area so that the automatic video instillator can be stably supported on the floor. The stand 34 is designed to function as an interface for connecting the automatic video instillator to other devices such as a syringe pump or dispenser.

A storage unit for storing the images captured by the image pickup unit 12 may be installed in the stand 34. The images may be selectively stored in the storage unit by an image storing switch 36.

A power connection unit 38 for supplying electric power required for driving the image pickup unit 12 and the image display unit 32 from an external side or for supplying electric power required for charging a battery 15 is provided on the stand 34. In addition, a connector 40 for connecting the syringe pump or dispenser, a USB connection terminal 43, and an image output terminal 44 are further provided on the stand 34.

The automatic video instillator further include an access port 46 for checking or replacing the administration unit 14 and the pushing member 20 when the administration unit 14 and the pushing member 20 operate abnormally.

Figure 7:
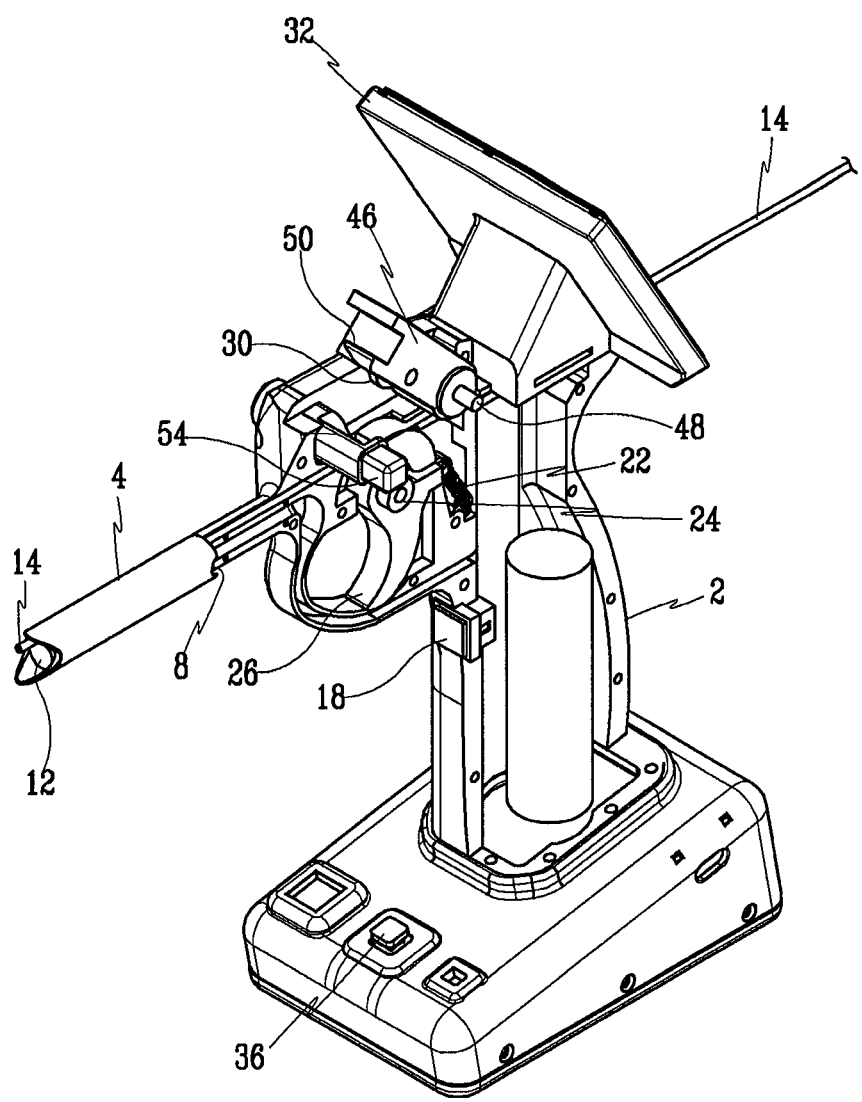
FIG. 7 is a perspective view of an internal structure of an automatic video instillator according to an exemplary embodiment of the present invention.
Figure 8:
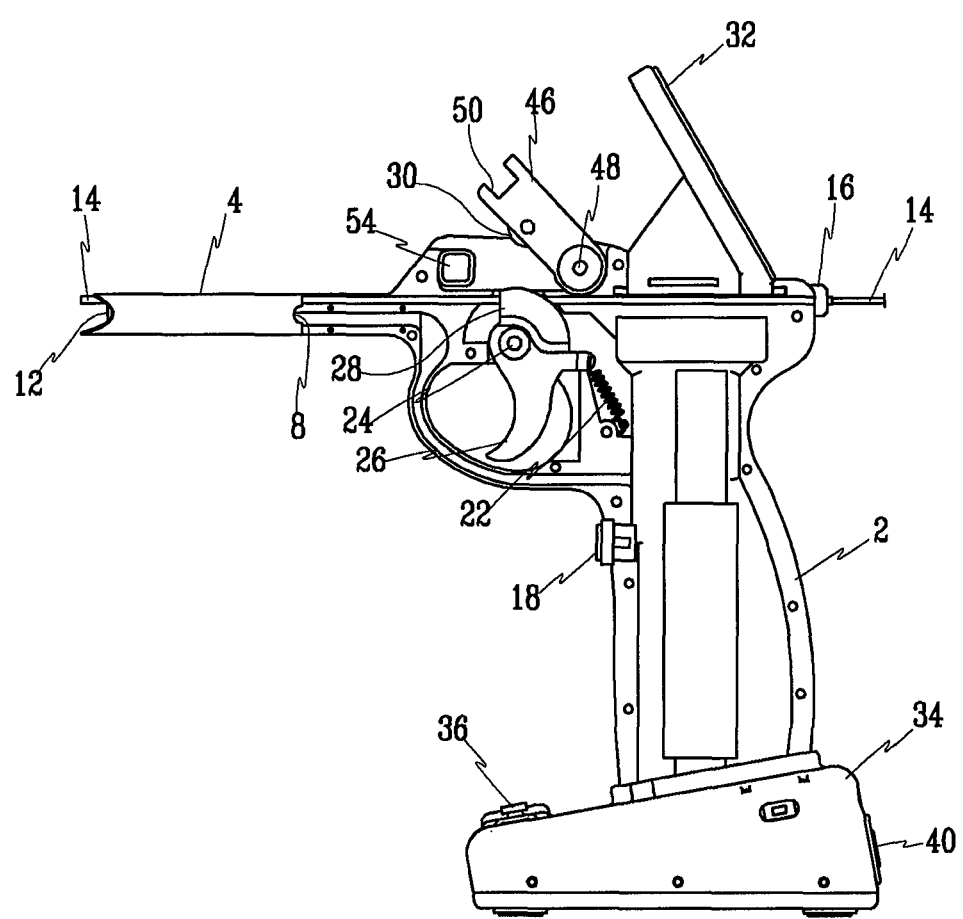
FIG. 8 is a side view of FIG. 7.
Figure 9:
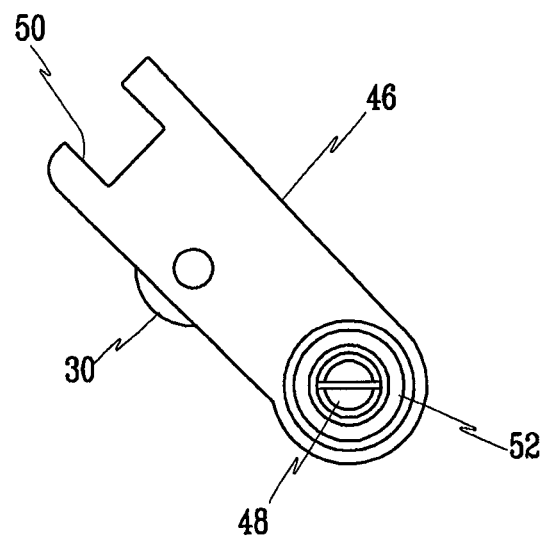
FIG. 9 is a view of an access port of an automatic video instillator according to an exemplary embodiment of the present invention.
Figure 10:
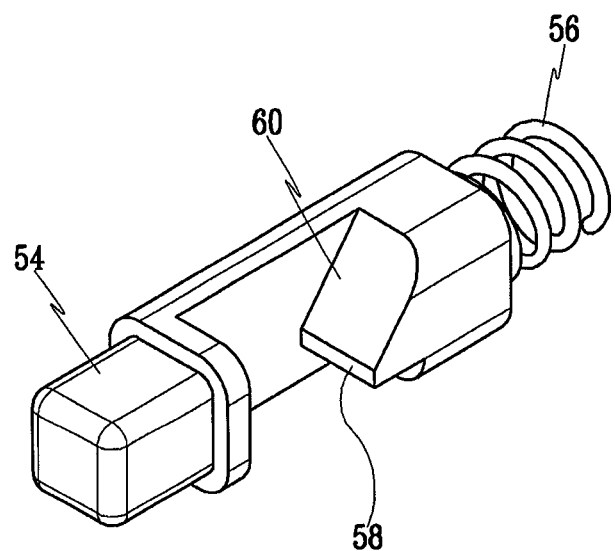
FIG. 10 is a view of an opening/closing button for opening and closing the access portion of FIG. 9.

As shown in FIGS. 7 and 8, the access port 46 is connected to the case 2 by a hinge shaft 48 formed on a first end thereof. A hooking portion 50 is formed on a second end of the access port 46. The access port 46 is opened by biasing a force of a torsion spring 52 disposed along an outer circumference of the hinge shaft 48.

The access port 46 is designed to be opened and closed by an opening/closing button 54. To realize this, the opening/closing button 54 is supported on the case 2 while being biased outward by an elastic member 56 and is provided at a side thereof with a hook step 58 corresponding to the hooking portion 50 of the access port 46.

When the access port 46 is closed, the hook portion 50 is hooked on the hook step 58 of the opening/closing button 54. When the opening/closing button 54 is pressed, the elastic member 56 is compressed and thus the hook portion 50 is released from the hook step 58. As a result, the access port 46 is opened by the elastic force of the torsion spring 52. When the access port 46 is closed, the torsion spring 52 is tensioned and a side of the access port 46 moves along an inclined surface 60 of the opening/closing button 54. Therefore, the opening/closing button 54 is pushed to one side so that the hook portion 50 is hooked on the hook step 48. Therefore, the closed state of the access port 46 is maintained.

In a state where the access port 46 is opened, abnormal operations of the administration unit 14 and the pushing member 20 can be checked and the administration unit 14 can be replaced.

In order to use the automatic video instillator, one of the guide units 4 and 4a is first selected in accordance with a species of the animal and installed on the case 2. That is, when the animal is the rodent, the straight guide unit 4 is used. When the animal is the primate, the curved guide unit 4 is used.

Next, the first end of the administration unit 14 is connected to the syringe pump or dispenser. In this state, the user inserts the guide unit 4 into the throat of the animal in a state where the user grasps the animal using one hand and grasps the case 2 using the other hand.

At this point, the image pickup unit 12 captures the images of portions in front of the guide unit 4 and transfers the images that are captured by the image pickup unit 12 to the image display unit 32. The user inserts the guide unit 4 into an optimal location of the throat while seeing the images displayed on the image display unit 32.

When the user inserts the guide unit 4 while seeing the images displayed on the image display unit 32, the airway of the animal can be sufficiently secured. When the airway of the animal is secured, the user pulls the lever 26 of the administration unit 14. Then, the lever 26 rotates about the axis of the hinge unit 24 while overcoming the biasing force of the elastic member 22. The rotation of the lever 26 rotates the actuating unit 28 to push the administration unit 14 out of the front end of the guide unit 4 by a predetermined distance.

By the above-described operation, the administration unit 14 is more deeply inserted into the airway of the animal. In this state, when the administration switch 18 is turned on, the inhalation stored in the syringe pump or dispenser is directed to the administration unit 14 and accurately administered into the airway of the animal.

When the lever 26 is released after the inhalation is administered, the lever 26 reversely rotates about the axis of the hinge unit 24 by the biasing force of the elastic member 22, and thus the actuating unit 28 rotates. As a result, the administration unit 14 returns to the initial position.

The above-described process is repeated to administer the inhalation to other animals.

During the above-described process, the image storing switch 36 may be turned on to store the images captured by the image pickup unit 12. At this point, electric power required for operating the automatic video instillator is supplied from the battery or an external power source connected to the power connection unit 38.

In addition, the image data on the administration of the inhalation can be stored in an external storage unit through the USB connection terminal 42 or the image output terminal 44 formed on the stand 34.

When the user sufficiently secures the optimal locations for the guide unit and the administration unit that are advanced into the airway while seeing the throat of the animal through the image display unit 32, the user can accurately administer the inhalation into the airway.

In addition, when the automatic video instillator malfunctions, the user opens the access port 46 by pressing the opening/closing button and identifies if the administration unit 14 and the pushing member 20 are operating abnormally.

What is claimed is:

1. An automatic video instillator comprising:
a case defining a space in which components are mounted;
a guide unit that protrudes frontward from the case to secure an airway of an animal by being inserted through a throat of the animal;
an image pickup unit that is installed on a front end of the guide unit to take images of portions in front of the guide unit;
an administration unit that is installed through the case and the guide unit to administer an inhalation;
an administration switch for adjusting administration of a predetermined amount of the inhalation directed to the administration unit into the airway of the animal;
an image display unit that is connected to the image pickup unit to allow a user to see images captured by the image pickup unit; and
a pushing member that is provided in the case to further push the administration unit frontward of the guide unit.

2. The automatic video instillator of claim 1, wherein the guide unit is detachably mounted on the case.

3. The automatic video instillator of claim 1, wherein the guide unit is formed in a straight shape or a curved shape.

4. The automatic video instillator of claim 1, wherein the image pickup unit is mounted such that a front end thereof is located in the guide unit.

5. The automatic video instillator of claim 1, wherein the pushing member includes a lever that is biased by an elastic member and fixed to the case by a hinge unit, an actuating unit that pushes the administration unit while contacting a first surface of the administration unit and being rotated by the operation of the lever, and a supporting wheel supporting a second surface of the administration unit.

6. The automatic video instillator of claim 1, wherein the image display unit is integrated with the case.

7. The automatic video instillator of claim 1, wherein the image display unit is detachably mounted on an outer side of the case.

8. The automatic video instillator of claim 1, wherein the image display unit is connected to the case by a cable.

9. The automatic video instillator of claim 1, wherein a stand is provided on the case to easily support the instillator on the floor.

10. The automatic video instillator of claim 9, wherein a storage unit for storing the images captured by the image pickup unit is provided in the case.

11. The automatic video instillator of claim 9, wherein an image storage switch for selectively storing the images captured by the pickup unit is provided on the stand.

12. The automatic video instillator of claim 9, wherein a power connection unit for supplying electric power required for driving the image pickup unit and the image display unit from an external side is provided on the stand.

13. The automatic video instillator of claim 12, wherein a power source required for driving the image pickup device and the image display unit is a primary or secondary battery.

14. The automatic video instillator of claim 9, wherein a USB connection terminal and an image output terminal are provided on the stand.

15. The automatic video instillator of claim 1, wherein the case is provided with an access port for checking the automatic video instillator.

16. The automatic video instillator of claim 1, wherein the image pickup unit is an electronic image pickup device and the electronic image pickup device is a charge coupled device.

17. The automatic video instillator of claim 1, wherein the administration unit includes one of a plastic tube and a fused silica capillary.

18. The automatic video instillator of claim 1, wherein the administration unit is of a push/pull sliding type that moves by a manual pushing/pulling operation.

19. An automatic video instillator comprising:
a case defining a space in which components are mounted;
a guide unit that protrudes frontward from the case to secure an airway of an animal by being inserted through a throat of the animal;
an image pickup unit that is installed on a front end of the guide unit to take images of portions in front of the guide unit;
an administration unit that is installed through the case and the guide unit to administer an inhalation;
an administration switch for adjusting administration of a predetermined amount of the inhalation directed to the administration unit into the airway of the animal;
an image display unit that is connected to the image pickup unit to allow a user to see images captured by the image pickup unit; and
a pushing member that is provided in the case to further push the administration unit frontward of the guide unit;
wherein the pushing member includes a lever that is biased by an elastic member and fixed to the case by a hinge unit, an actuating unit that pushes the administration unit while contacting a first surface of the administration unit 14 and being rotated by the operation of the lever, and a supporting wheel supporting a second surface of the administration unit.

20. The automatic video instillator of claim 19, wherein the actuating unit and the supporting wheel are formed of rubber or silicon that has a relatively high frictional force.

21. The automatic video instillator of claim 19, wherein the administration unit is driven by a gear-type lever and a gear-type actuating unit, or by a motor rotating the actuating unit about a hinge.

* * * * *